United States Patent [19]

Horiuchi et al.

[11] Patent Number: 4,507,390

[45] Date of Patent: Mar. 26, 1985

[54] CHROMATOGRAPHIC ANALYSIS FOR ANIONS INVOLVING COMPLEXING ANIONS WITH A POLYHYDRIC ALCOHOL

[75] Inventors: Susumu Horiuchi; Taiji Hiraoka; Toru Saito, all of Hitachi, Japan

[73] Assignee: Hitachi, Ltd., Tokyo, Japan

[21] Appl. No.: 243,620

[22] Filed: Mar. 13, 1981

[30] Foreign Application Priority Data

Mar. 13, 1980 [JP] Japan .................................. 55-32535
Mar. 26, 1980 [JP] Japan .................................. 55-39203

[51] Int. Cl.³ ...................... G01N 31/08; G01N 27/06
[52] U.S. Cl. ...................................... 436/161; 210/656; 422/70; 436/100; 436/133; 436/150
[58] Field of Search ............... 23/230 R; 127/46.2; 210/656; 436/100, 133, 149, 161, 182, 150

[56] References Cited

U.S. PATENT DOCUMENTS

| | | | |
|---|---|---|---|
| 2,818,851 | 1/1958 | Khym | 127/46.2 X |
| 3,468,764 | 9/1969 | Cohen | 436/182 |
| 4,242,097 | 12/1980 | Rich | 23/230 R |
| 4,272,246 | 6/1981 | Fritz | 23/230 R |
| 4,290,775 | 9/1981 | Stevens | 23/230 R |
| 4,314,823 | 2/1982 | Rich | 23/230 R |

OTHER PUBLICATIONS

J. X. Khym et al., J.A.C.S., 74, 2090-2094 (1952).

*Primary Examiner*—Sidney Marantz
*Attorney, Agent, or Firm*—Antonelli, Terry & Wands

[57] ABSTRACT

Process for analyzing anions in a liquid by means of an ion exchanger and by complex formation with specific anions by addition of polyhydric alcohol. Sensitivity is increased owing to the fact that the complex of specific anions with polyhydric alcohol has a high activity as acid.

19 Claims, 13 Drawing Figures

CHROMATOGRAPHIC ANALYSIS FOR ANIONS INVOLVING COMPLEXING ANIONS WITH A POLYHYDRIC ALCOHOL

BACKGROUNDS OF THE INVENTION

This invention relates to a process for analyzing anions, and particularly to a process for analyzing anions suitable for analyzing anions having a low degree of dissociation and a low electroconductivity such as borate ion and carbonate ion with high precision.

Recently, techniques of microanalysis of liquid waste have been advanced, and components on a ppm level can be analyzed in a short time with good precision. Particularly, the ion chromatography apparatus based on U.S. Pat. No. 3,897,213 can perform simultaneous analysis of many components on a pmm level within 30 minutes by separating cations such as sodium ion, potassium ion, etc., or anions such as chloride ion, nitrate ion, sulfate ion, etc. from one another by means of ion exchange resin and neutralizing an eluate with another kind of ion exchange resin, thereby leading only the desired kinds of ions to an electroconductivity type detector. However, it has been found as a result of studies made by the present inventors that the process of said U.S. Pat. No. 3,897,213 has such drawbacks that, since an electroconductivity type detector is used for detection, the ions having a high electroconductivity in an aqueous solution can be measured with a high sensitivity, but carbonate ion, or borate ion having a low degree of dissociation, that is, a low electroconductivity, has such a low sensitivity that it cannot be throughly analyzed.

SUMMARY OF THE INVENTION

An object of the present invention is to improve the sensitivity of anions to be analyzed.

The present invention is characterized by mixing a liquid to be analyzed with a substance capable of reacting with specific anions to be analyzed, thereby forming complexes with an increased activity as acid, and by measuring the activity of the mixed solution as the acid, thereby obtaining an amount of the specific anions.

As the specific anions to be analyzed, every kind of anion can be enumerated, and there are many anions having a high degree of dissociation and a high activity as acid without any treatment. It is not necessary to apply the present invention to these anions. Thus, the present invention is especially effective for anions having a low degree of dissociation and a low electro-conductivity in an aqueous solution, such as carbonate ion or borate ion.

As the substance capable of reacting with these anions to form complexes with an increased activity as acid, polyhydric alcohol is effective. That is, polyhydric alcohol reacts with an anion to form a complex, and the resulting increase in the number of H+ ions enhances the activity as acid. For example, boric acid undergoes reaction according to the following equation.

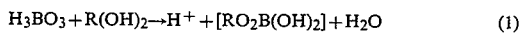

$$H_3BO_3 + R(OH)_2 \rightarrow H^+ + [RO_2B(OH)_2] + H_2O \qquad (1)$$

The activity as acid can be measured in various manners. The most ordinary method is to detect an electroconductivity.

For the above-mentioned reasons, anions can be analyzed according to the present invention with a sensitivity that is more than ten times that of direct analysis of anions.

BRIEF DESCRIPTION OF THE DRAWINGS

FIG. 2A shows analytical results of an aqueous 300 ppm boric acid solution, FIG. 2B analytical results of an aqueous 900 ppm boric acid solution, and FIG. 2C analytical results of an aqueous 1,500 ppm boric acid solution.

DETAILED DESCRIPTION OF THE PREFERRED EMBODIMENTS

Figure 1:
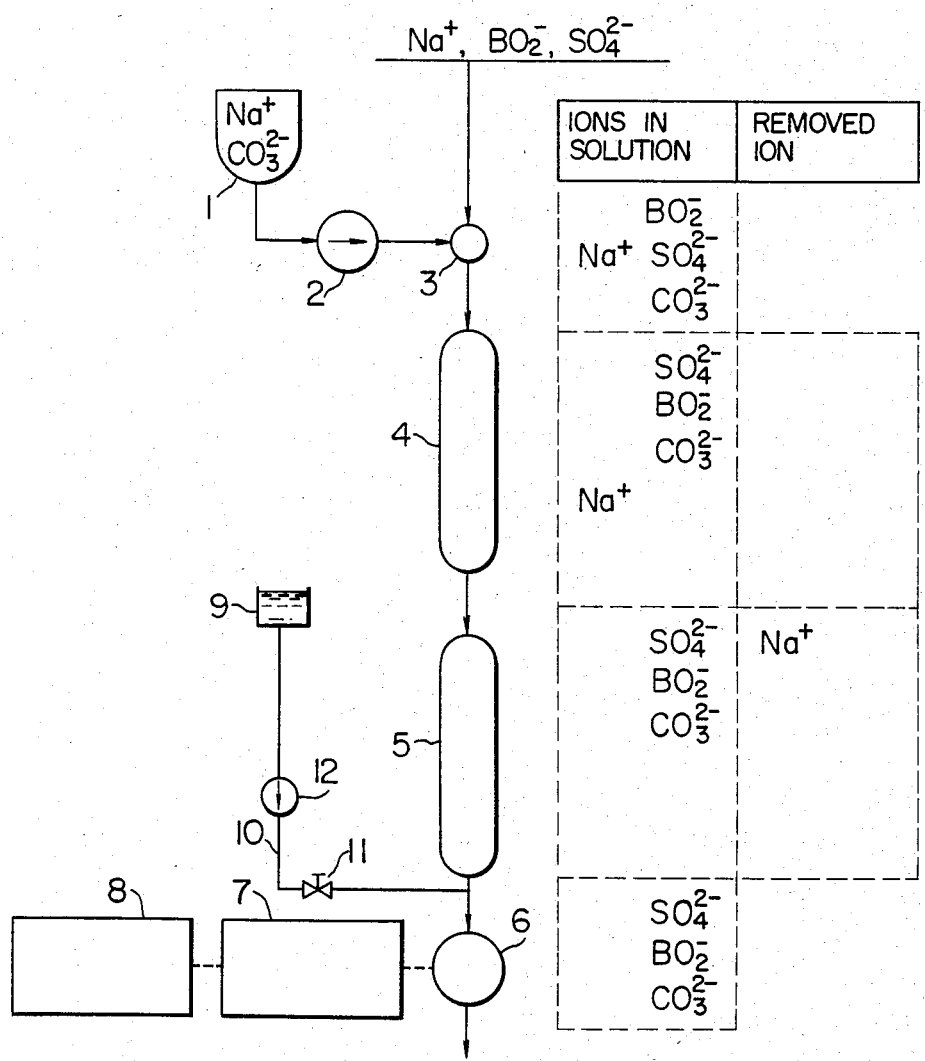
FIG. 1 is a flow diagram of an ion chromatography apparatus according to the present invention.

A flow diagram of a borate ion analyzer for a process for analyzing borate ions according to a preferred embodiment of the present invention is shown in FIG. 1. Ion chromatograph comprises an eluting solution tank 1 containing an eluting solution, a feed pump 2 for feeding the eluting solution at a constant rate, a sample injector 3 having a function to inject a predetermined amount of a sample, a separation column 4 for separating either ion species of cations or anions in the sample, a removal column 5 for adsorbing the ion species not separated in the separation columm, an electroconductivity type detector 7, an electroconductivity cell 6, and a recorder 8. The foregoing structure is the same as that of the conventional ion chromatography apparatus. In the present embodiment, a tank 9 containing polyhydric alcohol, a piping 10, a valve 11 and a pump 12 are added to the foregoing structure so that polyhydric alcohol can be added to the downstream side of the removal column 5.

In analyzing anions, an alkaline eluting solution, for example, an aqueous sodium hydroxide solution, or a mixed aqueous solution of sodium hydrogen carbonate and sodium carbonate, is used, and the separation column 4 is filled with OH−form anion exchange resin, and the removal column 5 is filled with H+form strongly acidic anion exchange resin. The sample solution introduced by the sample injector 3 is led to the separation column 4 and anions are separated from the sample solution by the anion exchange resin, and then the sample solution is led to the removal column 5. An eluting solution is fed to the separation column 4 with separated anions, and the anions are eluted from the anion exchange resin thereby. The eluting solution containing the anions flows out of the separation column 4 and are removed or neutralized in the removal column 5 according to the following reaction:

(I) When sodium hydroxide is used as the eluting solution.

$$R'.H^+ + NaOH \rightarrow R'.NA + H_2O \quad (2)$$

(II) When sodium carbonates are used as the eluting solution.

$$2R'.H^+ + Na_2CO_3 \rightarrow 2R'.Na + H_2CO_3 \quad (3)$$

$$R'.H^+ + NaHCO_3 \rightarrow R'.Na + H_2CO_3 \quad (4)$$

wherein R' represents ion exchange resin.

Carbonic acid is a weak acid, and thus its solution has a low electroconductivity.

In this manner, the eluting solution is removed or converted to substances having a low electroconductivity in the removal column 5, whereby the influence of the eluting solution upon the output of the detector is suppressed.

On the other hand, anions are changed to free acid in the separation column 5 in the following manner, $$R'.H^+ + Na^+Cl^- \rightarrow R'.Na + HCl \quad (5)$$

and detected in the electroconductivity type detector 7. This dominates the electroconductivity mainly due to H$^+$ or OH$^-$ having a high mobility.

Borate ion analysis using ion chromatography apparatus will be described in detail below. Borate ions exist together with other ion species Na$^+$, SO$_4^{2-}$, etc. in the sample solution. The sample solution is an aqueous solution containing the above-mentioned ion species. The sample solution is led to the separation column 4 through the sample injector 3. An aqueous sodium carbonate solution as the eluting solution in the eluting solution tank 1 is fed to the separation column 4 immediately after the feeding of the sample solution. The sample solution and the eluting solution pass through the separation column 4 and the removal column 5 substantially at the same time. The eluting solution has a function as a carrier for the sample solution and a function to desorb the anions adsorbed on the anion exchange resin in the separation column 4 and regenerate the anion exchange resin. Cations pass through the separation column 4 within a short time, whereas anions pass through the separation column 4 while repeating action of adsorption-desorption between the anion exchange resin under the influence of the action of the eluting solution. The degree of adsorption of anions depends upon the anion species. By supply of the test solution, the ion species in a mixed state at the inlet to the separation column 4 flow out of the separation column 4 in the order of Na$^+$, CO$_3^{2-}$, BO$_2^-$, and SO$_4^{2-}$, as shown at the right hand of the separation column 4 in FIG. 1. Anion species are separated also from one another in this manner.

In the removal column 5, cations in the sample solution and the eluting solution are removed by the removal column 5. The aqueous solution containing anions flows out of the removal column 5 and enters the electroconductivity type detector 7. Boric acid is a very weak acid in an aqueous solution, and its aqueous solution as it is has a low electroconductivity. Thus, the sensitivity of ion chromatography apparatus is low. That is, distinction is hardly made from sulfate ion and carbonate ion.

Borate ions at the outlet from the removal column 5 exist as boric acid, free acid, in the aqueous solution. Thus, complexes are formed by reaction of borate ions with polyhydric alcohol. The electroconductivity of the borate-polyhydric alcohol complex is high enough to enable detection with a high sensitivity. In the reaction of borate ions with polyhydric alcohol by neutralization titration, a molar ratio, reaction temperature, and reaction time can be freely selected. However, in the case of ion chromatography, apparatus extention of separated anion peaks must be minimized, and thus reaction time and reaction temperature are restricted. Particularly, the time required for migration of anions from the removal column 5 to the electroconductivity type detector 7 is a few to a few ten seconds in view of precisoin, that is, in view of minimizing the extension of separated anion peaks. However, generally, it has so far been regarded as difficult to form complexes at such a high speed, but only by mixing polyhydric alcohol into a sample existing between the removal column 5 and the position to detect the electroconductivity at room temperature, for example, by making the concentration of polyhydric alcohol to be mixed 0.5% by mole after the mixing, the detection sensitivity is about 70 times improved, as has been confirmed by tests. The present invention has been made on the basis of these test results.

Among polyhydric alcohols, mannitol, dulcitol, sorbitol, xylitol and fructose have a remarkable effect on improvement of electroconductivity, and other polyhydric alcohols such as sucrose, maltose, lactose, glucose, rhamnose, mannose, galactose, arabinose, xylose, erythritol, glycerol, propyleneglycol, trimethyleneglycol and ethyleneglycol are also effective. These substances react with borate ions to be analyzed and from complexes capable of elevating the activity as acid.

In the ion chromatograph, polyhydric alcohol is fed by a pump as an aqueous 0.1-2 mol.% solution of polyhydric alcohol, preferably an aqueous 0.5-1 mol.% solution, and mixed into the solution flowing out of the removal column 5. A mixing ratio by volume, as expressed by the following formula, is 0.2-2.0, preferably 0.5-1.0, but the present invention is not restricted thereto.

$$\text{Mixing ratio by volume} = \frac{\text{Aqueous alcohol polyhydric solution}}{\text{Effluent solution from removal column}}$$

By opening the valve 11 and driving the metering pump 12, the polyhydric alcohol in the tank is mixed into the sample, and reacts with borate ions to form complexes capable of elevating the activity as acid. The detector 7 measures the electroconductivity cell 6. The detector 7 measures the electroconductivity of each anion species, and the wave form having peaks in the order of CO$_3^{2-}$, BO$_2^-$ and SO$_4^{2-}$ is plotted on the recording paper as the results. When a specific anion species is mixed into the sample as a dummy, the peak by BO$_2^-$ can be securely obtained, and a BO$_2^-$ concentration can be known from the size of the peak.

The detector is not restricted only to the electroconductivity type detector, but measurement of electrode potential by H$^{3O}$ ions or OH$^-$ ions by means of glass electrode, etc., or detection of H$^+$ ions or OH$^-$ ions by addition of an indicator together with the polyhydric alcohol, resulting in color development, and colorimetry is also possible.

Piping 10 is connected to the downstream side of the removal column 5, because, if there are cations in the sample, no borate-polyhydric alcohol complexes are formed, and thus it is necessary to add polyhydric alcohol to the sample after the cations have been removed from the sample.

EXAMPLE 1

Borate ions were measured by using an chromatography apparatus ion shown in the above-mentioned embodiment.

Figure 2A:
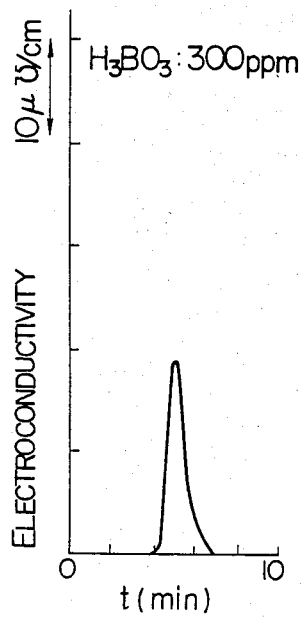
FIGS. 2A–2C show results of analyzing boric acid solutions according to the ion chromotography apparatus shown in FIG. 1, where
Figure 2B:
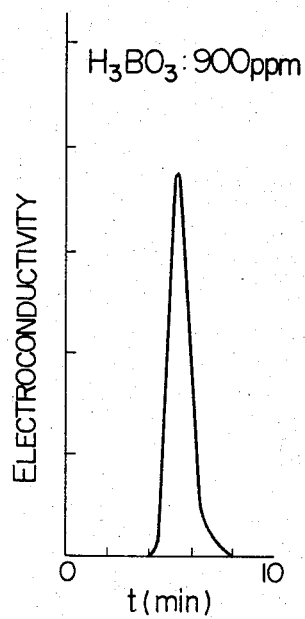
Figure 2C:
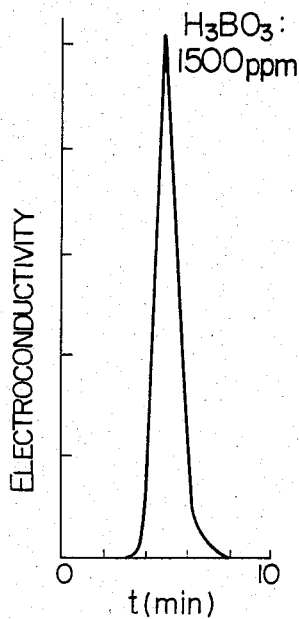

As an alkaline eluting solution, an aqueous solution of 0.03 M $NaHCO_3$ and 0.0024 M $Na_2CO_3$ was passed at 230 ml/min. A separation colummn, 3 mm in diameter and 500 mm high, as 4 and a removal column, 6 mm in diameter and 250 mm high, as 5 were used. 100 μl of a sample was injected into the separation column 4 from the sample injector 3. Then, immediately thereafter, the alkaline eluting solution was fed to the separation column 4, and a liquid effluent from the separation column 4 and the removal column 5 was obtained. An aqueous 1 M sorbitol solution was fed from the tank 9 through the piping 10 by the metering pump 12 at a rate of 230 ml/min. and mixed with the liquid effluent from the removal column 5. Chromatograms obtained by injecting 100 μl each of aqueous boric acid solutions having concentrations each of 300 ppm, 900 ppm and 1,500 ppm and containing the sorbitol are shown in FIGS. 2A, 2B and 2C. The sensitivity was about 70 times improved in the peak height ratio, as compared with the cases with no sorbitol. Borate ions in trace amounts such as on ppm level can be detected.

EXAMPLE 2

Figure 3:
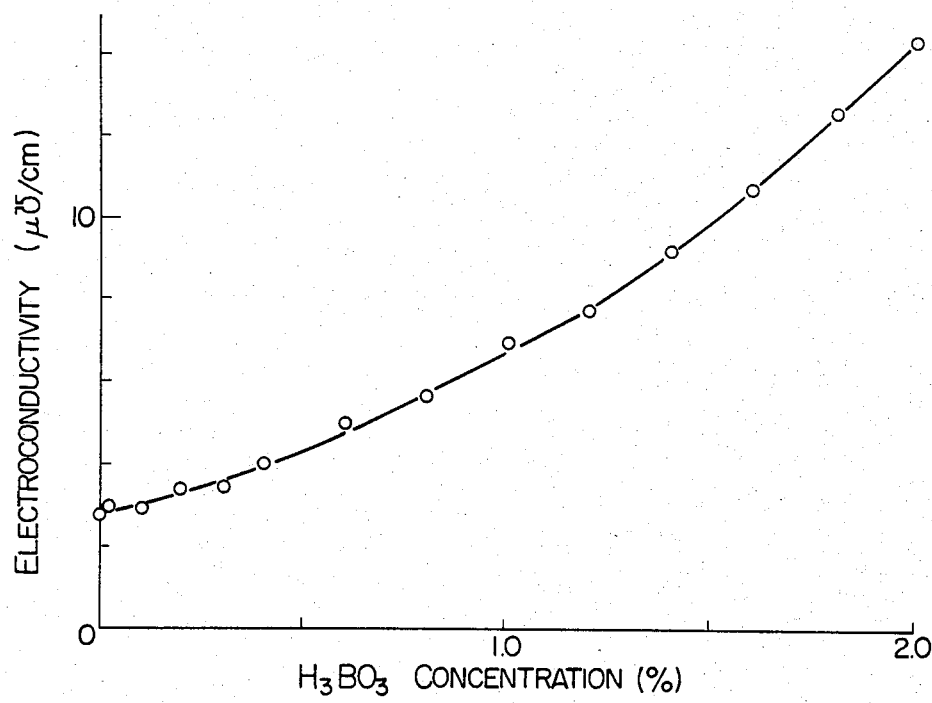
FIG. 3 is a characteristic diagram showing relationship between boric acid concentration and electroconductivity.
Figure 4:
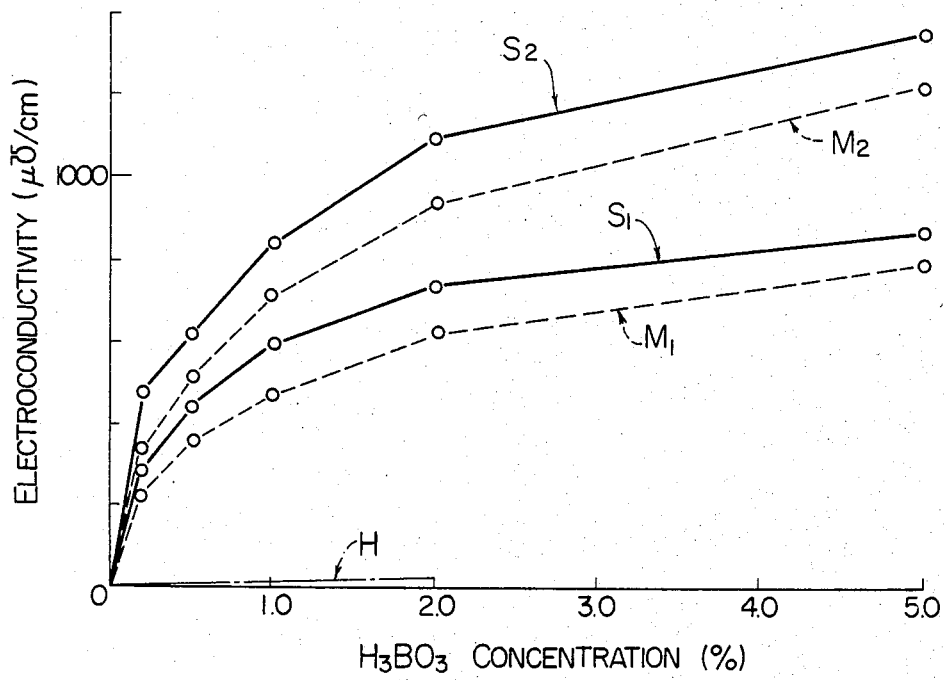
FIG. 4 is a characteristic diagram showing a relationship between boric acid concentration and electroconductivity when polyhydric alcohol is added.

Boric acid concentration of aqueous boric acid solutions were changed, and the electroconductivity of each solution was measured. Results are shown in FIG. 3. On the other hand, aqueous boric acid solutions each containing 0.5 M or 1.0 M polyhydric alcohol (sorbitol or mannitol) were prepared, and their electroconductivity was measured. Results are shown in FIG. 4. In FIG. 4, curve $M_1$ is a characteristic curve of the aqueous boric acid solution containing 0.5 M mannitol, curve $M_2$ is that of the boric acid solution containing 1.0 M mannitol, curve $S_1$ that of the aqueous boric acid solution containing 0.5 M sorbitol, and curve $S_2$ is that of the aqueous boric acid solution containing 1.0 M sorbitol. Curve H is that of only aqueous boric acid solution. As is evident from the diagram, the electroconductivity of a boric acid solution is remarkably increased by the presence of polyhydric alcohol.

EXAMPLE 3

Figure 5:
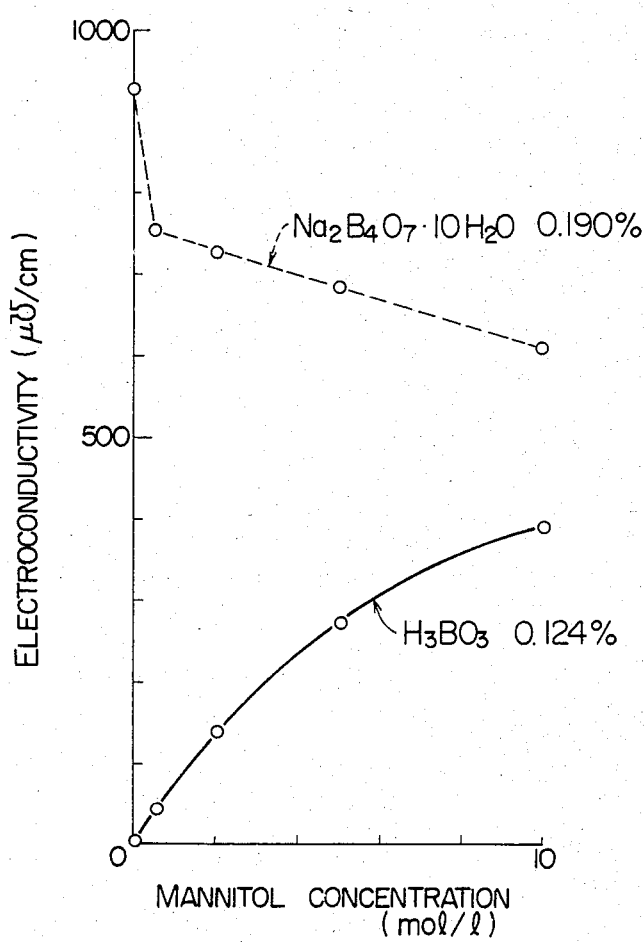
FIG. 5 is a characteristic diagram showing relationship between mannitol concentration and electroconductivity.

Electroconductivity of aqueous 0.124% boric acid solutions, each containing 0.05, 0.2 0.5 or 1.0 M mannitol was measured, and the results are shown in FIG. 5. In this case the electroconductivity is increased with increasing mannitol concentration. For comparison, electroconductivity of aqueous 0.190% sodium borate ($Na_2B_4O_7 \cdot 10H_2O$) solutions containing mannitol at the same concentrations as above was measured. The results are also shown in FIG. 5. As is seen from FIG. 5, in the latter case containing $Na^+$, the electroconductivity of the solutions was decreased with increasing mannitol concentration. The reasons why the cations in the sample are adsorbed in the removal column 5 and the anions are brought into a free acid state in the present invention are that the formation of borate-polyhydric alcohol complexes based on the reaction of borate ions with polyhydric alcohol is greatly influenced by the coexisting cations, as confirmed by tests shown in the present Example. By adding polyhdric alcohol to the liquid effluent from the removal column 5, the sensitivity is improved, and a trace amount of borate ions can be detected with high precision. The addition of polyhydric alcohol is effective for a liquid containing borate ions and no cations.

Positions of the separation column 4 and the removal column 5 in the borate ion chromatograph of FIG. 1 can be reversed with no adverse effect upon the analysis of borate ions.

When it is certain that no other ion species than borate ion are contained in a sample solution, it is not necessary to separate anion species from one another. Thus, the separation column can be omitted, leaving the removal column, and water can be used as the eluting solution. Since polyhydric alcohol is added to the sample solution flowing out of the removal column also in this case, the borate ions can be detected with high sensitivity.

Figure 6:
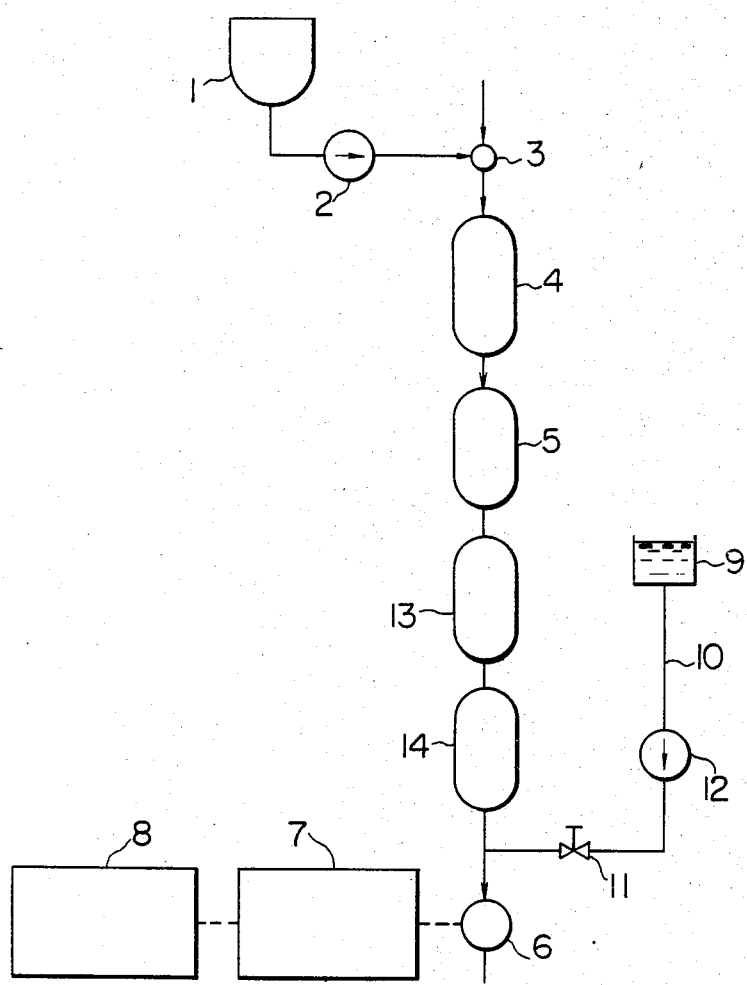
FIGS. 6 and 7 are flow diagrams showing further embodiments according to the present invention.

A flow diagram of a borate ion chromatography system according to another embodiment of the present invention is shown in FIG. 6 where the same members as in the embodiment of FIG. 1 are represented by the same numerals.

In the present embodiment, a silver column 13 and a post silver column 14 are arranged between the removal column 5 and the electroconductivity cell 6. Piping 10 is connected to the piping connecting the post silver column 14 to the electroconductivity cell 6. In the silver column 13 there are packings with adsorbed silver ions. The silver column 13 and the post silver column 14 have a function to remove chloride ions, when the liquid effluent from the removal column 5 contains chloride ions. The post silver column 14 is provided for backup of the silver column 13. If chloride ions are contained in a sample solution, analysis of borate ions becomes difficult. In the present embodiment, similar effect as in the embodiment of FIG. 1 can be obtained, and even if chloride ions are contained in the sample solution, borate ions can be detected with high precision.

Figure 7:
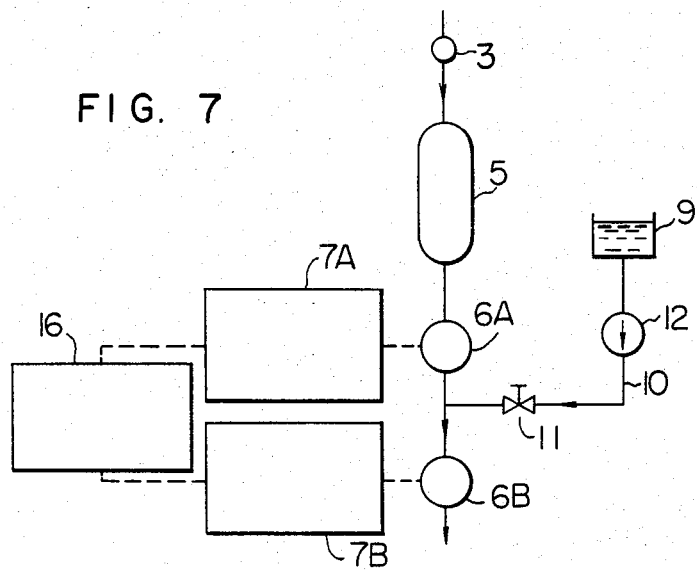

Further embodiment of the present invention will be described below, referring to FIG. 7, where the same members as in the embodiment of FIG. 1 are represented by the same numerals as in FIG. 1.

A sample solution containing borate ions and other anion species is fed to a removal column 5 through a sample injector 3. Cations in the sample solution are removed in the removal column 5. In the present embodiment, a plurality of anion species flow out of the removal column 5 not in the ordered sequence as in the embodiment of FIG. 1 but in a mixed state. When such sample solution reaches an electroconductivity cell 6A, electroconductivity $I_1$ in total of all anion species is measured by an electroconductivity type detector 7A. The measured value $I_1$ is put into a computer 16. Sorbitol as polyhydric alcohol in a tank 9 is added to the sample solution flowing out of the electroconductivity cell 6A. In the sample solution, borate-sorbitol complexes are formed by addition of sorbitol thereto, and when the sample solution reaches an electroconductivity cell 6B, electroconductivity $I_2$ in total of all anion species in the sample solution is detected by an electroconductivity type detector 7B. The measured value $I_2$ is put into the computer 16. The computer 16 calculates $(I_0=I_1-I_2)$. The value $I_0$ is an increment of electroconductivity based on the complexes formed between the added sorbitol and borate, and the borate ion concentration is known from the value $I_0$. If a working curve is obtained in advance, the borate ions in the sample solution can be quantitatively determined with high precision in the same manner as in the embodiment of FIG. 1. In this case, detectors based on the measurement of electrode potential or colorimetry can be used. In the case of colorimetry, an indicator must be added, not in mixture with polyhydric alcohol, but to the upstream side of the electroconductivity cell 6A. When no cations are obviously contained in a sample solution, the removal column 5 can be omitted.

In the foregoing embodiments, an activity as acid has been measured, but the amount of borate ions in a sample solution can be also determined by adding polyhydric alcohol to a sample solution containing borate ions to form complexes, then further adding a predetermined amount of an alkaline substance thereto, and measuring an excess alkalinity after the neutralization reaction. However, in this case the activity as acid is merely converted to the amount of another state of form, and is included in the scope of measuring an activity as acid.

A process for treating a radioactive liquid waste generated from a pressurized water type nuclear reactor utilizing the present invention will be described below.

Figure 8:
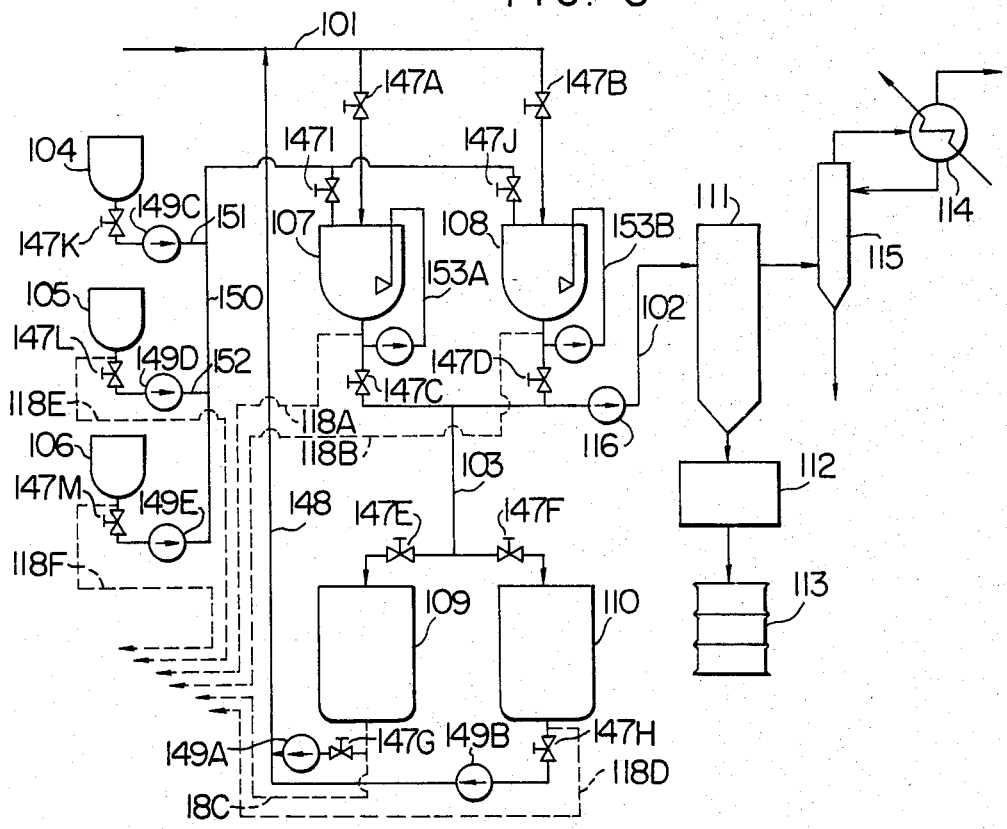
FIG. 8 is a flow diagram of an apparatus for treating a radioactive liquid waste, utilizing the present invention.
Figure 9:
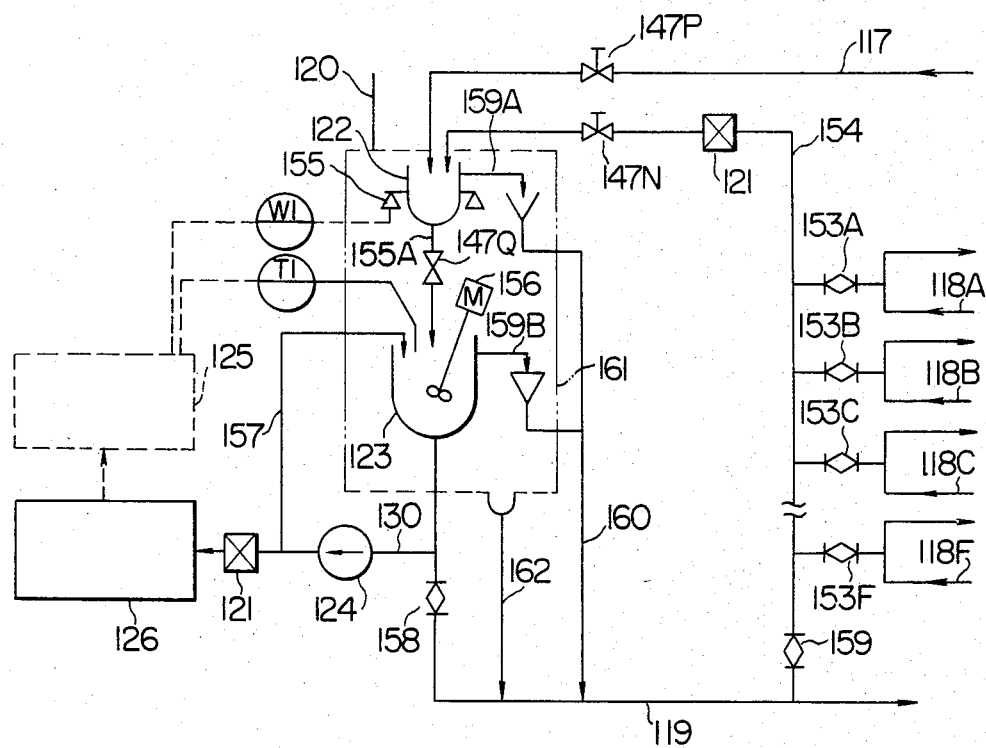
FIG. 9 is a detailed flow diagram of a dilution unit used in the apparatus of FIG. 8.

Preferred embodiment of it will be described, referring to FIGS. 8, 9, and 10.

The radioactive liquid waste generated from the pressurized water-type nuclear reactor is changed into powder in a centrifugal thin film drier, and the resulting powder is pelletized. However, the change of the radioactive liquid waste into powder is sometimes difficult to carry out, depending upon its composition. That is, the radioactive liquid waste generated from the pressurized water type nuclear reactor, that is, a radioactive liquid waste containing boric acid and sodium hydroxide, can be changed into powder in a centrifugal thin film drier, so far as a ratio of sodium hydroxide concentration/boric acid concentration by weight, which will be hereinafter referred to as "R value", is in a range of 0.28–0.4. Thus, if an R value of a radioactive liquid waste is outside the range of 0.28–0.4, the R value must be adjusted to within the above-mentioned range by adding sodium hydroxide or boric acid thereto. The following embodiment is to perform the above-mentioned operations.

Piping 101 is connected to liquid waste tanks 107 and 108 through valves 147A and 147B, respectively. Piping 102 provided at the liquid waste tanks 107 and 108 is connected to a centrifugal thin film drier 111 through a feed pump 116. Valves 147C and 147D are provided in piping 102. The centrifugal thin film drier 111 has a rotating shaft with a plurality of movable blades, inserted into a shell, and a heating jacket around the shell (not shown in the drawing), as disclosed in Japanese Kokai (Laid-open) Patent Application No. 87400/79. Numeral 112 is a pelletizer, 113 a drum, 114 a condenser, and 115 a mist separator. Piping 103 connected to the piping 102 is connected to storage tanks 109 and 110. Valves 147E and 147F are provided in the piping 103. Piping 148 connected to the piping 101 is connected to the storage tank 109 through a pump 149A and a valve 147G, and to the storage tank 110 through a pump 149B and a valve 147H. Piping 150 provided with valves 147I and 147J are connected to the liquid waste tanks 107 and 108. Piping 150 is connected to a sodium hydroxide tank 106 through a pump 149E and a valve 147M. An additive tank 104 is connected to the piping 150 through piping 151, a valve 147K and a pump 149C. A boric acid tank 105 is connected to the piping 150 through piping 152, a valve 147L and a pump 149D. Numerals 153A and 153B are circulation pipings for injecting the liquid waste for stirring in the liquid waste tanks 107 and 108. Pipings 118A, 118B, 118C, 118D, 118E and 118F are sampling pipes. The sampling pipes 118A, 118B, 118C, 118D, 118E and 118F are connected to piping 154 through switch valves 153A, 153B, 153C, . . . 153F, respectively. The piping 154 is connected to a weighing tank 122 through a filter 121 and a valve 147N. A pure water feed pipe 117 having a valve 147P is connected to the weighing tank 122. A weight meter 155 is provided at the weighing tank 122. Piping 155A provided at the weighing tank 122 is connected to a dilution tank 123 through a valve 147Q. A stirrer 156 is provided at the dilution tank 123. Piping 130 connects the dilution tank 123 to an ion chromatograph analyzer 126. A filter 121 and a pump 124 are provided in the line 130. A return pipe 157 to the dilution tank 123 is provided in the piping 130. A discharge pipe 119 having a valve 158 is connected to the piping 130. The piping 154 is connected to the piping 119. The discharge pipe 119 is connected to the piping 101. A valve 159 is provided in the piping 154. Numerals 159A and 159B are overflow pipes, and are connected to a discharge pipe 160. The discharge pipe 160 is connected to the discharge pipe 119. To a space 161 where the weighing tank 122 and the dilution tank 123 are arranged are connected a tank vent system 120, and also a drain piping 162. Numeral 125 is a computer.

Figure 10:
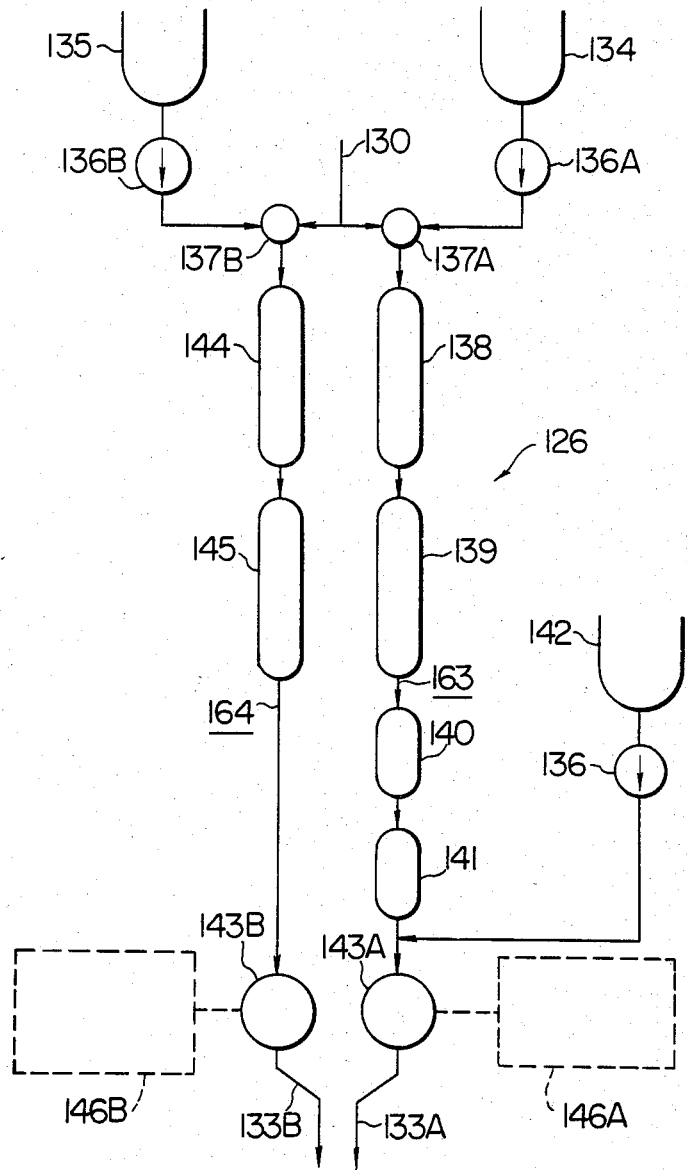
FIG. 10 is a system diagram of an ion chromatography analyzer shown in FIG. 9.

Detailed structure of the ion chromatograph analyzer 126 is shown in FIG. 10. The ion chromatograph analyzer 126 comprises an anion analyzer section 163 and a cation analyzer section 164. In the anion analyzer section 163, an anion separation column 138 filled with anion exchange resin, a removal column 139 filled with cation exchange resin, a silver column 140 with adsorbed silver ions, a post silver column 141, and an electroconductivity cell 143A are arranged in successive connection from a switch cock 137A toward the downstream side. Sorbitol tank 142 is connected to the downstream side of the post silver column 141. To the switch cock 137A is connected a tank 134 filled with an alkaline eluting solution through a metering pump 136A. In the cation analyzer section 164, a cation separation column 144 filled with cation exchange resin, a removal column 145 filled with anion exchange resin, and an electroconductivity cell 143B are arranged in successive connection from the switch cock 137B towards the downstream side. A tank 135 filled with an acidic eluting solution is connected to the switch cock 137B through a pump 136B. Electroconductivity detectors 146A and 146B are provided at the electroconductivity cells 143A and 143B, respectively. Pipings 133A and 133B connected to the electroconductivity cells 143A and 143B, respectively, are connected to the discharge pipe 119 of FIG. 9. Piping 130 is connected to the switch cocks 137A and 137B.

Radioactive liquid waste generated from a pressurized water type nuclear reactor is fed to the liquid waste tank 107 through the piping 101. The valve 147A is open, while the valve 147B is closed. A detection signal from liquid level meters (not shown in the drawing) provided at the liquid waste tanks 107 and 108 is put into the computer 125. All the operations of the present embodiment are carried out automatically by the computer 125.

Figure 11:
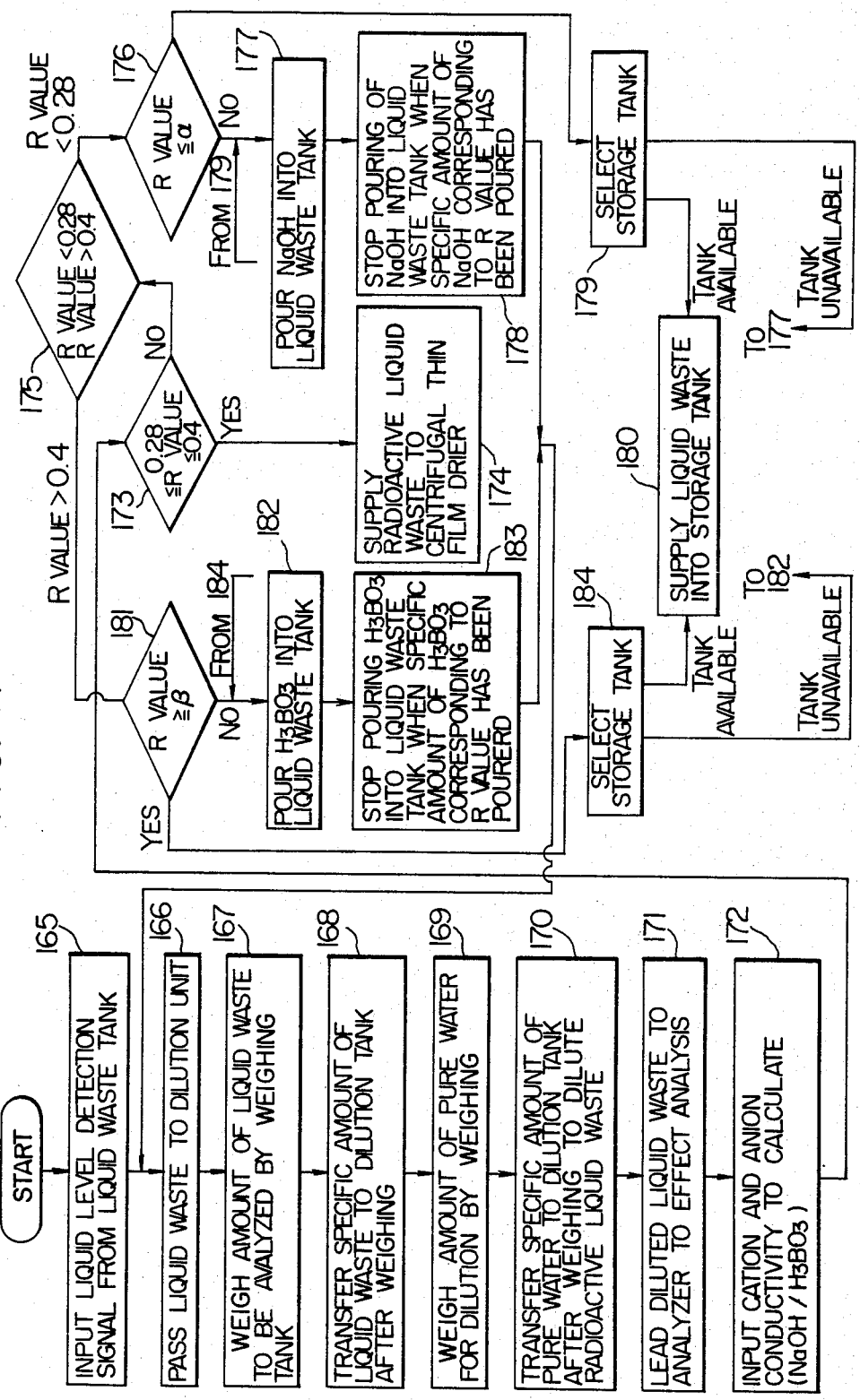
FIG. 11 is a flow chart showing operation of a computer shown in FIG. 9.

FIG. 11 shows operations to be carried out by the computer 125. The computer 125 detects the increasing liquid level in the liquid waste tank, and opens the valve in the corresponding sampling pipe. In this case, since a liquid level increase in the liquid waste tank 107 is detected (step 165), the computer 125 opens the valve 153A and pass the radioactive liquid waste from the liuqid waste tank 107 to the weighing tank 122, the dilution tank 123 and the discharge pipe 119 (step 166). The valves 153B–153F are closed, whereas the valve 147N is open. Before the passage of the radioactive liquid waste, pure water is fed to the weighing tank 122, the dilution tank 123 and the discharge pipe 107 from the pure water supply pipe 147 to complete washing them. After the operations of step 166 has been conducted for a predetermined period of time, the amount of the radioactive liquid waste to be analyzed is weighed (step 167). The weighing is carried out in the weighing tank 122, and the signal of the weighing meter 155 is put into the computer 125. When the radioactive liquid waste in the weighing tank 122 reaches a predetermined amount, the valve 147Q is made open by the instructions from the computer 125, an at the same time the valves 147N and 153A are closed. The radioactive liquid waste in the weighing tank 122 is led to the dilution tank 123 (step 168). After the radioactive liquid waste in the weighing tank 122 has been discharged, the valve 147Q is closed, and the valve 147P is closed. Pure water is fed into the weighing tank 122 from the pure water feed pipe 117, and a predetermined amount of pure water is weighed (step 169). The computer 125 closes the valve 147P and opens the valve 147Q when the pure water in the weighing tank 122 reaches the predetermined amount. The weighed pure water is fed into the dilution tank 123 (step 170). The stirrer 156 is actuated, so that the radioactive liquid waste and pure water are stirred and mixed. After the predetermined period of time, the pump 124 is made to run by the instruction from the computer 125, and the diluted radioactive liquid waste is led to the ion chromatograph analyzer 126 through the filter 121 and analyzed (step 171).

Analytical operations in the ion chromatograph analyzer 126 will be briefly described below, referring to FIG. 10. By manipulation of switch cocks 137A and 137B having a function to make a definite volume of sampling, a sample (diluted radiaoctive liquid waste) is supplied from the piping 130 to the anion separation column 138 and the cation separation column 144. The anion separation column 138 separates and adsorbs anions including borate ions in the sample. The cations remaining in the sample are adsorbed by the removal column 139. By driving the pump 136A and switching the switch cock 137A, an alkaline eluting solution is fed into the anion separation column 138. The anions adsorbed by the anion separation column 138 are released and eluted in the order of weaker ionic strength. The cations in the eluate are removed by the removal column 139. Chloride ions (whose releasability is close to that of borate ions) are removed from the eluate by the silver column 140. The eluate leaving the post silver column having the same functio as the silver column 140 is admixed with sorbitol from the tank 142 by driving the pump 136. Sorbitol forms complex ions with borate to improve the electroconductivity. The electroconductivity of the eluate is measured in the electroconductivity cell 143A by means of the electroconductivity detector 146A. The measured value of electroconductivity is put into the computer 125.

On the other hand, the sample fed into the cation separation column 144 is freed from the cations including sodium ions by the cation separation column 144. The anions in the sample are removed by the removal column 145. By driving the pump 136B and switching the switch cock 137B, an acidic eluting solution is fed into the cation separation column 144. The cations adsorbed by the cation separation column 144 are released and eluted in the order of weaker ionic strength. The electroconductivity of the eluate is measured by the electroconductivity detector 146B, and put into the computer 125. The liquid waste discharged from the electroconductivity cells 143A and 143B are discharged into the discharge pipe 119.

The electroconductivity measured by the analyzer 126 is put into the computer 125, which calculates an R value from the electroconductivity (step 172). In step 173, the following relationship (6) is judged.

$$0.28 \leqq R \text{ value} \leqq 0.4 \tag{6}$$

If an R value is within the range of relationship (6), the valve 147C is made open by the instructions from the computer 125, and the pump 116 is driven to introduce the radioactive liquid waste from the liquid waste tank into the centrifugal thin film drier 111 through the piping 102 (step 174). The radioactive liquid waste fed into the shell of the centrifugal thin film drier 111 is heated, and is made into powder by revolution of movable blades occasioned by the revolution of rotating shaft. The water vapor generated from the centrifugal thin film drier 111 is freed from the entrained mists by the mist separator 115 and condensed in the condenser 114. The powder is led to the pelletizer 112 and shaped into pellets. The pellets are filled into the drum 113 and solidified by pouring asphalt or plastics into the drum 113. By adding a binder from the additive tank 104, the strength of pellets can be increased.

If the R value is outside the range of relationship (6), condition (R value <0.28) or (R value >0.4) is judged in step 175. In the case of (R value <0.28), the following condition is judged in step 176.

$$R \text{ value} \leqq \alpha \tag{7}$$

where $\alpha$ must satisfy the condition ($\alpha < <0.28$).

When the R value fails to satisfy the condition (7) in step 176 ($\alpha < R$ values $<0.28$), a composition-adjusting solution (sodium hydroxide) is poured into the liquid waste tank from the sodium hydroxide tank 106 (step 177). The amount of sodium hydroxide to be poured is determined in accordance with the R value, and its amount is increased with smaller R value. After a predetermined amount of sodium hydroxide has been poured, the pouring of sodium hydroxide into the liquid waste tank is discontinued (step 178). After the adjustment of the composition, the radioactive liquid waste in the liuqid waste tank 107 is analyzed. That is, the valves 153A and 147N are made open, and operations from step 166 to step 173 are repeated. After it has been confirmed as a result of analysis that the condition (6) is satisfied, operation of step 174 for powder formation is carried out.

Treatment in the case of satisfying the condition (7) in step 176 will be described below. A storage tank is selected for tentatively storing the radioactive liquid waste having an R value less than the predetermined value α, that is, the liquid waste containing a large amount of boric acid (step 179). The measured value of the liquid level detectors provided at the storage tanks 109 and 110 is put into the computer 125, and the computer 125 selects a storage tank 109 or 110 capable of storing the radioactive liquid waste from the measured value. The valves 147C and 147E are made open, and the radioactive liquid waste is fed into the storage tank 109 (step 180). When it is judged in step 179 that the storage tank 109 or 110 is full of the radioactive liquid waste, it becomes impossible to feed the radioactive liquid waste into the storage tanks 109 and 110, and operation of step 177 is carried out.

When the condition (R value >0.4) is judged in step 175, the following condition (8) is judged in step 181, $$\text{R value} > \beta \tag{8}$$

where $\beta$ must satisfy the condition ($\beta \gg 0.4$).

When the R value fails to satisfy the condition (8) ($\beta > \text{R value} > 0.4$), a composition-adjusting solution (boric acid) is poured from the boric acid tank 105 into the liquid waste tank 107 (step 182). The amount of boric acid to be poured is increased with larger R value. After a predetermined amount of boric acid has been poured, its supply is discontinued (step 183). To confirm the R value after the adjustment, operations from step 166 to step 173 are repeated. When the condition (6) is satisfied, operation of step 174 is carried out.

When it is judged that the condition (8) is satisfied in step 181, selection of storage tank (step 184) is carried out in the same manner as in the case that the condition (7) is satisfied, and a radioactive liquid waste containing much sodium hydroxide and having an R value larger than 0.4 as the second set value is fed into a specific storage tank, for example, storage tank 109 (step 180). In the storage tanks 109 and 110, the radioactive liquid waste having a considerably large R value and the radioactive liquid waste having a considerably small R value are mixed together.

When the storage tanks 109 and 110 have no room for the storage, operation of step 182 is carried out.

Analysis of the radioactive liquid waste in the storage tanks 109 and 110 where the radioactive liquid waste having a considerably large R value and the radioactive liquid waste having a considerably small R value are mixed together (mixed radioactive liquid waste) is carried out. Operations from step 166 to step 173 are carried out. When the mixed radioactive liquid waste fails to satisfy the condition (7), the mixed radioactive liquid waste is transferred to the liquid waste tank 107 or 108, and then boric acid or sodium hydroxide is added thereto to adjust the composition. The mixed radioactive liquid waste satisfying the condition (7) is fed into the centrifugal thin film drier 111 and changed into powder. For adjusting the composition of a radioactive liquid waste containing much boric acid or sodium hydroxide, a large amount of the composition-adjusting solution is required.

In the present embodiment, the necessary amounts of boric acid and sodium hydroxide for the composition djustment can be considerably reduced by mixing a radioactive liquid waste containing considerably much boric acid with a radioactive liquid waste containing considerably much sodium hydroxide among the radioactive liquid wastes intermittently generated from a pressurized water type nuclear reactor. For example, in the case of excess sodium hydroxide having an R value of 1.0, the amount of powder formed becomes about three times that from the non-adjusted liquid waste when the composition is adjusted by adding sulfuric acid to the liquid waste. In the present embodiment, no such increase in powder amount appears, and the amount of powder formed by the centrifugal thin film drier 111 is considerably reduced. All the amount of the radiotive liquid waste generated from the pressurized water type nuclear reactor is not stored, and so large facility for storing the radioactive liquid waste is not required.

By using the ion chromatograph analyzer 126, boric acid having a low ionization tendency can be analyzed in the radioactive liquid waste having various components without any influence of interfering substances.

What is claimed is:

1. A process for analyzing anions, which comprises feeding a liquid containing a plurality of free acids as anions to a first column filled with anion exchange resin, thereby separating the free acids by the anion exchange resin, then feeding an alkaline eluting solution to the first column, thereby releasing the free acids from the first column, introducing the liquid containing the free acids into a second column filled with cation exchange resin, mixing a liquid containing the free acids flowing out of the second column with a polyhydric alcohol, and measuring the activity as acid of the mixed liquid.

2. A process according to claim 1, wherein the free acids to be analyzed is borate ions.

3. A process according to claim 2, wherein the activity as acid to be measured is electroconductivity.

4. A process for analyzing anions, which comprises feeding a liquid containing at least one species of cations and specific anions to be analyzed to a first column filled with anion exchange resin, thereby separating the anions by the anion exchange resin, then feeding an alkaline eluting solution to the first column, thereby releasing the anions from the first column, introducing the liquid containing the anions into a second column filled with cation exchange resin to remove cations from the liquid introduced into the second column, measuring a first activity as acid of the liquid, freed from the cations, flowing from the second column, mixing the liquid, containing the anions, flowing out of the second column with a polyhydric alcohol, measuring a second activity as acid of the mixed liquid, and determining an amount of the specific anions from the first and second activities.

5. A process according to claim 4, wherein the specific anions are borate ion.

6. A process according to claim 5, wherein the activity as acid to be measured is electroconductivity.

7. A process for analyzing anions, which comprises feeding a liquid containing anions and at least one species of cations to a first column filled with anion exchange resin, thereby separating the anions by the anion exchange resin, then feeding an alkaline eluting solution to the first column, thereby releasing the anions from the first column, introducing the liquid containing the anions into a second column filled with cation exchange resin to thereby remove cations from the liquid, mixing a liquid containing the anions, flowing out of the second column, with a polyhydric alcohol, the polyhydric alcohol being an aqueous 0.1–2 mol % solution of polyhydric alcohol, and measuring the activity as acid of the mixed liquid, thereby determining an amount of at least one specific anion.

8. A process according to claim 7, wherein the at least one specific anion is borate ion.

9. A process according to claim 8, wherein the activity as acid to be measured is electroconductivity.

10. A process according to claim 1, 4 or 7, wherein said polyhyrdic alcohol is selected from the group consisting of mannitol, dulcitol, sorbitol, xylitol, fructose, sucrose, maltose, lactose, glucose, rhamnose, mannose, galactose, arabinose, xylose, erythritol, glycerol, propyleneglycol, trimethyleneglycol and ethyleneglycol.

11. A process according to claim 10, wherein said polyhydric alcohol is selected from the group consisting of mannitol, dulcitol, sorbitol, xylitol, and fructose.

12. A process for analyzing anions, which comprises feeding a liquid containing anions and at least one species of cations to a first column filled with anion exchange resin, thereby separating the anions by the anion exchange resin, then feeding an alkaline eluting solution to the first column, thereby releasing the anions from the first column, introducing the liquid containing the anions into a second column filled with cation exchange resin to thereby remove cations from the liquid, mixing a liquid, containing the anions, flowing out of the second column with a polyhydric alcohol, the polyhydric alcohol being an aqueous 0.5-1.0 mol % solution of polyhydric alcohol, and measuring the activity as acid of the mixed liquid, thereby determining an amount of at least one specific anion.

13. A process for analyzing anions in a liquid containing anions and cations, which comprises feeding said liquid containing anions and cations to a first column filled with anion exchange resin, thereby separating the anions by the anion exchange resin, then feeding an alkaline eluting solution to the first column, thereby releasing the anions from the first column, introducing the liquid containing the anions and cations into a second column filled with cation exchange resin, thereby removing said cations from said liuqid, mixing and reacting said liquid containing the anions flowing out of the second column, after removal of said cations, with a polyhydric alcohol, said polyhydric alcohol mixed with said liquid being an aqueous 0.1-2 mol % solution of polyhydric alcohol, and measuring a property of the mixed and reacted liquid, whereby the amount of anions in said liquid can be determined.

14. A process according to claim 13, wherein said property is electroconductivity.

15. A process according to claim 13, wherein said property is electrode potential by $H^+$ or $OH^-$ ions by means of a glass electrode.

16. A process according to claim 13, wherein said property is colorimetry after addition of an indicator for $H^+$ or $OH^-$ ions to said liquid.

17. A process according to claim 12 or 13, wherein said polyhydric alcohol is mixed with said liquid at a mixing ratio by volume of 0.2-2.0, where $$\text{mixing ratio by volume} = \frac{\text{aqueous polyhydric alcohol solution}}{\text{Said Liquid}}$$

18. A process according to claim 17, wherein said mixing ratio by volume is 0.5-1.0.

19. A process for analyzing anions, which comprises feeding a liquid containing anions and at least one species of cations, as well as chloride ions, to a first column filled with an anion exchange resin, thereby separating the anions by the anion exchange resin, then feeding an alkaline eluting solution to the first column, thereby releasing the anions from the first column, introducing the liquid containing the anions into a second column filled with cation exchange resin to thereby free the liquid from the cations, passing the liquid, after having the cations removed therefrom, through a silver column to remove chloride ions from the liquid, mixing the liquid containing the anions flowing out of the silver column with a polyhydric alcohol, and measuring the activity as acid of the mixed liquid, thereby determining an amount of at least one specific anion.

* * * * *